(12) United States Patent
Schneider et al.

(10) Patent No.: US 12,402,829 B2
(45) Date of Patent: Sep. 2, 2025

(54) DEVICES AND METHODS FOR DETERMINING ANOSMIA AND/OR AGEUSIA

(71) Applicant: CONTEMPORARY HEALTH SYSTEMS, LLC, West Palm Beach, FL (US)

(72) Inventors: Ira Schneider, Palm Beach, FL (US); Robert J. Fish, West Palm Beach, FL (US)

(73) Assignee: CONTEMPORARY HEALTH SYSTEMS, LLC, West Palm Beach, FL (US)

( * ) Notice: Subject to any disclaimer, the term of this patent is extended or adjusted under 35 U.S.C. 154(b) by 0 days.

(21) Appl. No.: 18/620,839

(22) Filed: Mar. 28, 2024

(65) Prior Publication Data
US 2024/0324944 A1   Oct. 3, 2024

Related U.S. Application Data

(60) Provisional application No. 63/493,121, filed on Mar. 30, 2023.

(51) Int. Cl.
*A61B 5/00* (2006.01)
*A23L 27/00* (2016.01)
(Continued)

(52) U.S. Cl.
CPC ............ *A61B 5/4017* (2013.01); *A23L 27/00* (2016.08); *A24F 40/30* (2020.01); *A61B 5/4011* (2013.01);
(Continued)

(58) Field of Classification Search
CPC ... A61J 7/0053; A61J 7/0023; A61K 2300/00; A61K 31/047; A61K 31/05;
(Continued)

(56) References Cited

U.S. PATENT DOCUMENTS

| 513,924 | A | * | 1/1894 | Hartnett | ............... | A61M 16/104 |
| | | | | | | 128/205.16 |
| 3,743,088 | A | * | 7/1973 | Henkin | .................... | A61B 5/00 |
| | | | | | | 422/503 |

(Continued)

FOREIGN PATENT DOCUMENTS

| WO | 0012411 A2 | 3/2000 |
| WO | 03105696 A1 | 12/2003 |

OTHER PUBLICATIONS

De Rosa Anna et al., "The flavor test is a sensitive tool in identifying the flavor sensorineural dysfunction in Parkinson's disease", Neurological Sciences (Testo Stampato), Springer Verlag, Milan, IT, vol. 40, No. 7, Mar. 20, 2019 (Mar. 20, 2019), pp. 1351-1356.

(Continued)

*Primary Examiner* — Annette Dixon
(74) *Attorney, Agent, or Firm* — FINNEGAN, HENDERSON, FARABOW, GARRETT & DUNNER LLP

(57) ABSTRACT

Systems, devices, and methods for determining anosmia and/or ageusia in a subject. are provided. Devices may include a housing, a composition stored within the housing, and an applicator. The composition may include one or more active ingredients and one or more inactive ingredients, the one or more active ingredients including a flavoring agent that may include salt, sour, sweet, or bitter taste and odor properties. The composition may be configured to remain stable. The housing may include a back pressure mechanism. The applicator may be configured to remove a predetermined amount of the composition from the housing and deliver the predetermined amount of the composition to one or more of a nose and a mouth of the subject.

22 Claims, 10 Drawing Sheets

(51) Int. Cl.
  *A24F 40/30* (2020.01)
  *A61L 27/00* (2006.01)
  *A61M 15/00* (2006.01)
(52) U.S. Cl.
  CPC . *A61M 15/0086* (2013.01); *A61B 2560/0418* (2013.01)
(58) Field of Classification Search
  CPC .. A61K 31/352; A61K 31/616; A61K 36/185; A61K 36/886; A61K 38/40; A61K 38/47; A61K 47/10; A61K 47/36; A61K 47/38; A61K 9/0014; A61K 9/0043; A61K 9/0053; A61K 9/006; A61K 9/008; A61K 9/06; A61K 9/12; A61K 9/127; A61K 9/5123; A61K 2800/88; A61K 33/16; A61K 33/20; A61K 49/0004; A61K 8/21; A61K 8/33; A61K 8/34; A61K 8/347; A61K 8/35; A61K 8/36; A61K 8/37; A61K 8/40; A61K 8/46; A61K 8/49; A61K 8/4926; A61K 8/494; A61K 8/4973; A61K 8/498; A61K 8/4986; A61K 8/922; A61M 11/002; A61M 11/06; A61M 15/0016; A61M 15/0018; A61M 15/0086; A61M 15/009; A61M 16/0078; A61M 16/0084; A61M 16/0666; A61M 16/0816; A61M 16/0858; A61M 16/101; A61M 16/104; A61M 16/1055; A61M 16/1065; A61M 16/208; A61M 2202/0208; A61M 35/006; A61P 11/02; A61P 11/04; A61P 23/00; A61P 29/00; A61P 31/04; A63B 2208/12; A63B 23/18; C12Y 302/01017; A23L 27/00; A24F 40/30; A45D 2200/1018; A46B 11/001; A46B 11/0055; A46B 13/02; A46B 2200/1066; A46B 9/04; A61B 10/0051; A61B 2010/0019; A61B 2560/0418; A61B 5/00; A61B 5/16; A61B 5/4011; A61B 5/4017; A61B 5/411; A61B 5/4866; A61B 5/6887; A61B 5/742; A61B 5/7435; A61B 50/31; A61C 1/0015; A61C 17/0202; A61C 17/227; A61C 19/04; A61C 19/06; A61Q 11/00; A61Q 13/00; A63F 2250/024; B65D 25/04; B65D 43/14; G01N 33/0001; G06Q 30/0281; G16H 20/13; G16H 20/60
  See application file for complete search history.

(56) References Cited

U.S. PATENT DOCUMENTS

| | | | | |
|---|---|---|---|---|
| 3,852,432 | A | | 12/1974 | Henkin |
| 4,526,273 | A | * | 7/1985 | Tsuji ..................... A45D 40/24 206/39.6 |
| 4,648,398 | A | * | 3/1987 | Agdanowski ..... A61M 16/0666 128/207.18 |
| 5,397,193 | A | * | 3/1995 | Kirk, III .............. A45D 40/267 401/122 |
| 5,496,537 | A | * | 3/1996 | Henry ................... A61K 31/05 424/464 |
| 5,584,285 | A | * | 12/1996 | Salter ..................... A61M 11/06 128/203.23 |
| 5,951,468 | A | * | 9/1999 | Orr ........................ A61B 5/4211 600/300 |
| 6,453,900 | B1 | * | 9/2002 | Barnes, Jr. ......... A61M 15/0086 239/338 |
| 10,531,722 | B2 | * | 1/2020 | Kukreja ............... A45D 40/265 |
| 10,610,147 | B2 | | 4/2020 | Albers |
| 11,297,926 | B2 | * | 4/2022 | Berhault .............. A45D 40/265 |
| 2002/0029779 | A1 | * | 3/2002 | Schmidt ............. A61M 16/208 128/205.25 |
| 2010/0180891 | A1 | * | 7/2010 | McKinnon ........ A61M 16/0078 128/205.24 |
| 2012/0321570 | A1 | * | 12/2012 | Kutsch .................. A61K 33/16 433/136 |
| 2017/0000744 | A1 | * | 1/2017 | Kaufman ............... A61K 9/006 |
| 2017/0247145 | A1 | | 8/2017 | Reisacher |
| 2022/0016266 | A1 | | 1/2022 | Schneider |
| 2022/0313710 | A1 | * | 10/2022 | Latefi ..................... A61K 38/40 |
| 2023/0248297 | A1 | | 8/2023 | Albers et al. |

OTHER PUBLICATIONS

Notification of Transmittal of the International Search Report and The Written Opinion of the International Search Authority for corresponding Application No. PCT/US2024/022059, filed Mar. 28, 2024, date of mailing Jul. 16, 2024, 18 pages.

Examination Notice in corresponding Hong Kong Standard Patent (O) Application No. 22024089521.3, filed Apr. 2, 2024, date of mailing Feb. 27, 2025, 7 pages.

Elena Gotkine, At-Home Smell Test Can Help ID Risk for Cognitive Impairment, HealthDay, published Apr. 2, 2025, 2 pages.

* cited by examiner

ACUTE Clinical Assessment

ON THE FIELD (1st Scan)

With each of the four applicator wands:

1. Olfactory: with mouth closed, place applicator directly beneath nostril for 5 seconds; record response.

Part 1 of 2: Olfactory (circle appropriate response)
0 = smells nothing or incorrect response
1 = identifies correct scent

| #1 | #2 | #3 | #4 |
|---|---|---|---|
| 0  1 | 0  1 | 0  1 | 0  1 |

Olfactory Total: _____

Add Olfactory and Gustatory Totals: ☐

2. Gustatory: with nose clamped, apply applicator to both lips equally, instruct subject to lick their lips; record response.

Part 2 of 2: Gustatory (circle appropriate response)
0 = tastes nothing or incorrect response
1 = identifies correct taste

| Watermelon | Mint | Vanilla | Coffee |
|---|---|---|---|
| 0  1 | 0  1 | 0  1 | 0  1 |

Gustatory Total: _____
Administered by: _____
Date: _____

IN THE MEDICAL TENT (2nd Scan)

With each of the four applicator wands:

1. Olfactory: with mouth closed, place applicator directly beneath nostril for 5 seconds; record response.

Part 1 of 2: Olfactory (circle appropriate response)
0 = smells nothing or incorrect response
1 = identifies correct scent

| #1 | #2 | #3 | #4 |
|---|---|---|---|
| 0  1 | 0  1 | 0  1 | 0  1 |

Olfactory Total: _____

Add Olfactory and Gustatory Totals: ☐

2. Gustatory: with nose clamped, apply applicator to both lips equally, instruct subject to lick their lips; record response.

Part 2 of 2: Gustatory (circle appropriate response)
0 = tastes nothing or incorrect response
1 = identifies correct taste

| Watermelon | Mint | Vanilla | Coffee |
|---|---|---|---|
| 0  1 | 0  1 | 0  1 | 0  1 |

Gustatory Total: _____
Administered by: _____
Date: _____

IN THE LOCKER ROOM (3rd Scan)

With each of the four applicator wands:

1. Olfactory: with mouth closed, place applicator directly beneath nostril for 5 seconds; record response.

Part 1 of 2: Olfactory (circle appropriate response)
0 = smells nothing or incorrect response
1 = identifies correct scent

| #1 | #2 | #3 | #4 |
|---|---|---|---|
| 0  1 | 0  1 | 0  1 | 0  1 |

Olfactory Total: _____

Add Olfactory and Gustatory Totals: ☐

2. Gustatory: with nose clamped, apply applicator to both lips equally, instruct subject to lick their lips; record response.

Part 2 of 2: Gustatory (circle appropriate response)
0 = tastes nothing or incorrect response
1 = identifies correct taste

| Watermelon | Mint | Vanilla | Coffee |
|---|---|---|---|
| 0  1 | 0  1 | 0  1 | 0  1 |

Gustatory Total: _____
Administered by: _____
Date: _____

FIG. 9

Periodic Evaluation Record

| Clinical Assessment S C O R E S | | | | | | | | | |
|---|---|---|---|---|---|---|---|---|---|
| 8 | | | | | | | | | |
| 7 | | | | | | | | | |
| 6 | | | | | | | | | |
| 5 | | | | | | | | | |
| 4 | | | | | | | | | |
| 3 | | | | | | | | | |
| 2 | | | | | | | | | |
| 1 | | | | | | | | | |
| 0 | | | | | | | | | |
| | ON THE FIELD | IN THE TENT | LOCKER ROOM | EXAM DATE* ____ | EXAM DATE* ____ | EXAM DATE* ____ | EXAM DATE* ____ | EXAM DATE* ____ | EXAM DATE* ____ |

Record the olfactory and gustatory totals as determined on each Clinical Assessment.

*TIBSDOS = Time Interval Between Scans To Be Determined On Site

FIG. 10

CHRONIC Periodic Evaluation Record

Date of Injury: _____ (if any)

With each of the four applicator wands:
1. Olfactory: with mouth closed, place applicator directly beneath nostril for 5 seconds; record response.

Part 1 of 2: Olfactory (circle appropriate response)
0 = smells nothing or incorrect response
1 = identifies correct scent 2. Gustatory: with nose clamped, apply applicator to both lips equally, instruct subject to lick their lips; record response.

Part 2 of 2: Gustatory (circle appropriate response)
0 = tastes nothing or incorrect response
1 = identifies correct taste

| Examination Date | Vial #1 No Yes | Vial #2 No Yes | Vial #3 No Yes | Vial #4 No Yes | Olfactory Subtotal | Vial #1 Watermelon | Vial #2 Mint | Vial #3 Vanilla | Vial #4 Coffee | Gustatory Subtotal | Olf + Gus TOTAL |
|---|---|---|---|---|---|---|---|---|---|---|---|
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |
| | 0  1 | 0  1 | 0  1 | 0  1 | | 0  1 | 0  1 | 0  1 | 0  1 | | |

For each examination, record the olfactory and gustatory totals as determined on each Clinical Assessment.
*TIBSDOS = Time Interval Between Scans To Be Determined On Site

FIG. 11

DEVICES AND METHODS FOR DETERMINING ANOSMIA AND/OR AGEUSIA

CROSS-REFERENCE TO RELATED APPLICATIONS

This application claims the benefit of priority to U.S. Provisional Application No. 63/493,121, filed Mar. 30, 2023, the contents of which is incorporated herein by reference in its entirety.

TECHNICAL FIELD

The present disclosure is related to devices, systems, and methods for determining anosmia (a loss of smell) and/or ageusia (a loss of taste) in a subject and/or stimulating recovery of a loss of smell and/or taste in a subject based on the four components of taste and smell (e.g., salt, sour, sweet, and bitter taste or odor properties), also known as the four corners of taste and smell. The loss of smell and/or taste may indicate a symptom of a medical condition or disease. Further, the loss of smell and/or taste may be used as guidance in preventative or rehabilitative medicine.

BACKGROUND

Traditional or conventional systems and methods for evaluating individuals with olfactory dysfunction (e.g., anosmia, hyposmia, dysosmia) and gustatory dysfunction (e.g., ageusia, hypogeusia, dysgeusia) involve ancillary assessments such as smell assessments (including orthonasal and retronasal assessments) and imaging (e.g., computed tomography (CT), magnetic resonance imaging (MRI)). However, such assessments do not provide the identification of particular odor or taste properties of the "four components of taste and smell" (e.g., salt, sour, sweet, and bitter) or the design and capabilities to assess and track sensory changes (e.g., deterioration or improvement) over time due to, for example, difficulties reproducing the same odor or taste properties over time/multiple uses (thus failing to reduce variables associated with the odor or taste properties of the assessments themselves changing) and difficulties reducing user, subject, and/or administrator biases. Further, traditional or conventional systems and methods require complex and expensive assessment processes and specialized equipment.

Changes in an individual's sense of smell and taste over time may also be an early indication of various neurological and/or cerebral medical conditions. Non-limiting examples of such neurological and/or cerebral medical conditions may include viral infection (e.g., COVID-19), bacterial infection, epilepsy, concussion, traumatic brain injury (TBI), repetitive brain/head injury (RHI), chronic traumatic encephalopathy (CTE), Parkinson's disease, Alzheimer's disease, dementia, rheumatoid arthritis, cystic fibrosis, diabetes, breast cancer metastasis, and multiple sclerosis. Various studies show that the loss of smell and/or taste may be early indicators of those neurological and/or cerebral medical conditions because these medical conditions (which are exemplary and non-limiting) may damage olfactory sensory neurons, causing a perceived loss of taste and/or smell. For example, the damage of glial cells (cells that provide physical and chemical support to neurons and maintain their environment) can cause local neurons to no longer function properly. The damage to glial cells may occur due to a buildup of toxins in a region of cellular damage or a direct loss of insulating myelin sheath (due to, for example, damage of the myelin sheath), which may result in the axon of a sensory neuron no longer conducting efficiently. This may result in a weakened signal at an axon terminal, and that weakened signal may not be sufficient to overcome a threshold that triggers neurotransmission. Therefore, a signal may not reach the brain for interpretation of: (1) whether a smell or taste is detected; and (2) what the taste or odor properties of the smell or taste are. Some medical conditions, such as cardiovascular disease, have also been associated with olfactory dysfunction.

Thus, there is a need for a non-invasive assessment of pre-clinical cognitive and sensory functioning that can be used as a diagnostic screener, longitudinal assessment tool, and treatment outcomes indicator.

SUMMARY

Embodiments consistent with the present disclosure provide both smell (odor, olfactory) and taste (flavor, gustatory) identification and perception diagnostic assessments based on scientifically, neurologically, and physiologically recognized four components (or four corners) of taste and smell (four odorants and flavors of salt, sour, sweet, and bitter). The four odorants and flavors are physiologically, neurologically, and anatomically present in the normative human and can be evaluated by embodiments of the devices, compositions, kits, and methods in accordance with the present disclosure without the need for any invasive procedure. The odor and flavor identification of the disclosed dual-use and multi-purpose devices, compositions, kits, and methods, may be performed contiguously in as little as five minutes, by either professionals or non-professionals.

Consistent with disclosed embodiments, a sense indicator device is provided. The sense indicator device may include a housing, a composition stored within the housing, and an applicator. The composition may include one or more active ingredients and one or more inactive ingredients. The one or more active ingredients may be in a concentration less than or equal to 3%; the one or more inactive ingredients may be in a concentration greater than or equal to 97%. The composition may be configured to remain stable. The applicator may be configured to remove a predetermined amount of the composition from the housing and deliver the predetermined amount of the composition to one or more of a nose and a mouth of a subject. The housing may include a back pressure mechanism configured to apply a pressure on the applicator as the applicator is removed (e.g., withdrawn, extracted) from the housing.

Consistent with disclosed embodiments, a method for determining one or more of a loss of taste and a loss of smell in a subject is provided. The method may comprise removing an applicator of a sense indicator device from a housing of the sense indicator device. The applicator may include a tip that retains a predetermined amount of a composition by passing through a back pressure mechanism. The method may comprise providing the applicator to one or more of a nose and a mouth of the subject, and one or more of a loss of smell and a loss of taste may be determined using a response of the subject to the provided applicator. In some embodiments, the response of the subject to the provided applicator may be recorded on an evaluation sheet. The applicator may be provided to the subject at predetermined intervals over an extended period of time (e.g., one year), and the response of the subject may be recorded on the evaluation sheet each time the applicator is provided to the subject. The evaluation sheet may score each response of the subject (e.g., based on one or more positive and negative responses), and serial changes in the sense of smell and/or taste in the subject may be evaluated via the recorded scores on the evaluation sheet.

BRIEF DESCRIPTION OF THE DRAWINGS

The accompanying drawings, which are incorporated in and constitute a part of this specification, illustrate disclosed embodiments and, together with the description, serve to explain the disclosed embodiments. The particulars shown are by way of example and for purposes of illustrative discussion of embodiments of the present disclosure. The description taken with the drawings makes apparent to those skilled in the art how embodiments of the present disclosure may be practiced.

FIG. 9 illustrates a first example of a scorable system evaluation sheet used for acute clinical assessment, consistent with embodiments of the present disclosure.

FIG. 10 is a second example of a scorable system evaluation sheet used for periodic evaluations, consistent with embodiments of the present disclosure.

FIG. 11 is a third example of a scorable system evaluation sheet used for chronic evaluations, consistent with embodiments of the present disclosure.

DETAILED DESCRIPTION

Embodiments of the present disclosure relate to devices, systems, and methods for determining a loss of taste and/or smell in a subject. More particularly, embodiments of the present disclosure relate to devices, systems, and methods for determining acute, moderate, and chronic anosmia (loss of smell) and/or ageusia (loss of taste) in individuals using the four components of taste and smell (salt, sour, sweet, bitter).

Embodiments of the present disclosure may be used to identify acute anosmia and/or ageusia, which may be an early indication of various neurological and/or cerebral medical conditions. Additionally, or alternatively, embodiments of the present disclosure may be used to track an individual's sense of smell and taste over time (e.g., in a longitudinal analysis).

Further, embodiments of the present disclosure may be used to stimulate recovery of a loss of smell and/or taste over time. Of the five most recognized human senses, the only two senses that can heal or improve are the senses of taste and smell. For example, exposure to odor and taste properties consistent with the four components of taste and smell (salt, sour, sweet, bitter), consistent with embodiments of the present disclosure, may agitate glial cells (e.g., as a noxious stimulus), causing the glial cells to proliferate and the local neurons to regain function.

In some embodiments of the present disclosure, a plurality of ingredients may be combined to form a unique composition, referred to generally as a sense indicator composition, for smell (odor, olfactory) and taste (flavor, gustatory) identification and perception. The use of "sense" is well known in the biology field as relating to a body perceiving an external stimulus. Although there may be more, the five main human senses relate to vision, hearing, smell, taste, and touch. As used herein, the term "sense indicator" or "sense indicator device" may refer to a composition or device that detects a state of two of the five main senses (e.g., taste and smell). Compositions and devices disclosed herein, therefore, may be indicators of a deterioration or improvement in an individual's sense of smell and/or taste when, for example, the composition and/or device is applied/provided to the individual's nose or mouth in different environments and/or at different times/days.

Figure 1:
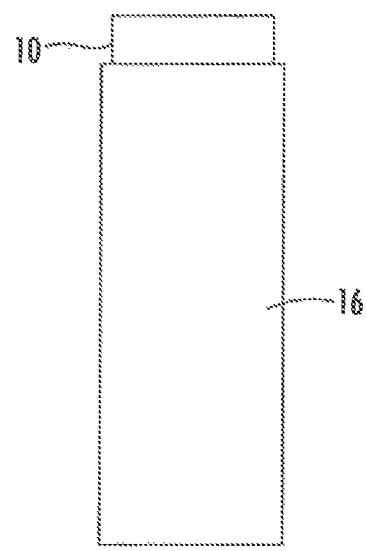
FIG. 1 illustrates an example of a sense indicator device, consistent with embodiments of the present disclosure.

The sense indicator compositions may comprise taste (flavor) and/or aroma (odor) properties to assess/track sensory perceptions of taste and/or smell. As discussed above, the sense indicator composition 10 may be used as an indicator of a medical condition or disease in which loss of taste and/or smell is a symptom of that medical condition or disease. For example, the medical condition or disease may cause a loss of smell and/or taste. As shown in FIG. 1, sense indicator composition 10 may be a solid and stored within housing 16 of the sense indicator device of FIG. 1. Although FIG. 1 illustrates a solid form of sense indicator composition 10, it is contemplated that the sense indicator composition may be in any suitable form, such as solid, liquid (e.g., viscous), and/or gas. Sense indicator composition 10 may be provided to an individual who is suspected of having one or more medical conditions or diseases as discussed above, or to an individual who is perceived to be healthy. Thus, in the latter, the providing of sense indicator composition 10 to detect, determine, and/or track a sense of smell and/or taste may be used in preventative care or early detection of such medical conditions or diseases.

Figure 2:
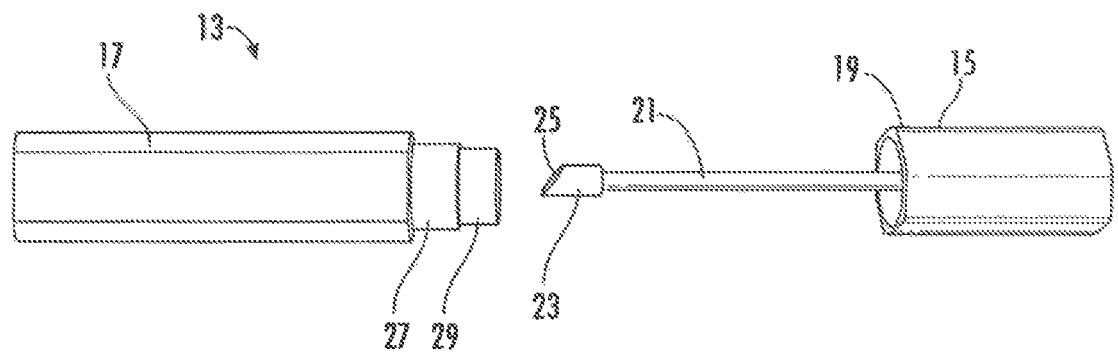
FIG. 2 illustrates another example of a sense indicator device, including a housing and an applicator, consistent with embodiments of the present disclosure.

Referring to FIG. 2, a sense indicator composition may be stored in sense indicator device 13. Sense indicator device 13 may include a housing with an upper portion 15 and lower portion 17. Lower portion 17 may include a cylindrical body 27 that holds the sense indicator composition in a liquid form (e.g., viscous material). Upper portion 15 may include lid 19, and an applicator. The applicator may include applicator wand 21 and applicator tip 23, where applicator tip 23 may include an angled portion 25. Lid 19 may mate with cylindrical body 27 via threading, where cylindrical body 27 includes external threads 29 and lid 19 includes internal threads (not shown). Although mating via threads is discussed with respect to FIG. 2, it is contemplated that any suitable mating mechanism may be used to mate upper portion 15 and lower portion 17 of the housing of sense indicator device 13. Non-limiting examples of such mating mechanisms include snap fit connections and tapered connections. Further, although lower portion 17 of sense indicator device 13 holding the sense indicator composition is shown as cylindrical in FIG. 2, it is contemplated that the component storing the sense indicator composition may be any suitable shape.

Figure 3:
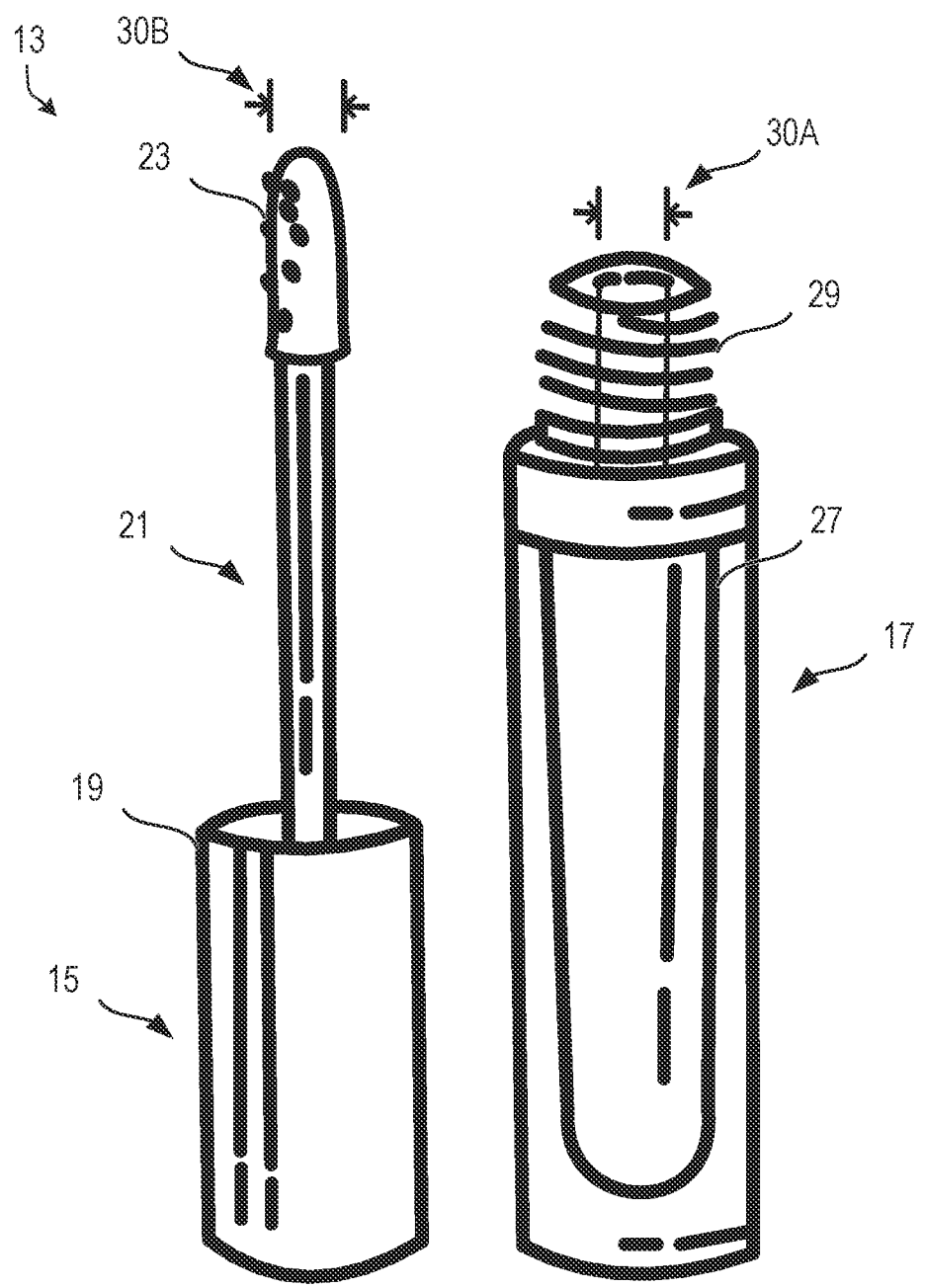
FIG. 3 illustrates a diagrammatic representation of a sense indicator device, consistent with embodiments of the present disclosure.

As shown in FIG. 3, in some embodiments, lower portion 17 of the housing of sense indicator device 13 may include a back pressure mechanism that controls the amount of the sense indicator composition that remains on tip 23 when removed from cylindrical body 27. The predetermined amount of sense indicator composition that remains on tip 23 may be selected based on: an amount of the composition necessary to induce a response (detection and/or identification of taste and/or smell) in a healthy individual; and/or an amount of composition that allows the composition to be used multiple times over a period of time (for example, a year). The back pressure mechanism may contribute to improvements over traditional systems and methods by providing the embodiments disclosed herein with the ability to reproduce the same odor and/or taste properties over time/multiple uses, by, for example, providing a consistent amount of the sense indicator composition with each use. The amount of sense indicator composition that remains on tip 23 may be controlled by a particular angle for angled portion 25 (as shown in FIG. 2) of tip 23. The back pressure mechanism may involve a portion of the cylindrical body (for example, an interior portion of external threading 29) being circumferentially or diametrically smaller than the circumference or diameter of applicator tip 23. For example, diameter 30A of an opening of cylindrical body 27 may be smaller than diameter 30B of applicator tip 23. When a user removes the applicator from the cylindrical body, the applicator tip 23 may experience friction when it mates with the narrower portion of the cylindrical body. Thus, a pressure may build in a backward direction (away from the applicator tip, toward the bottom of the cylindrical body) that must be overcome to remove the applicator tip 23 from the cylindrical body 27. Excess composition on the applicator tip 23 may be removed as the applicator tip 23 is pulled out of the cylindrical body and the built up back pressure is overcome. Thus, the back pressure mechanism may remove excess composition on applicator tip 23 such that a desired amount remains on tip 23. Further, in some embodiments, applicator tip 23 may be made of a sponge or microfiber material such that the material of tip 23 absorbs an additional amount of the composition or is able to compress through the interior portion of external threading 29.

Further, the sense indicator composition may include particular odor and/or taste properties. For example, the sense indicator composition may include an odor and/or taste property of salt, sweet, sour, or bitter. As discussed above, such odor and/or taste properties may correspond to one or more of the four components of taste or smell (salt, sweet, sour, bitter). The particular odor and/or taste properties of the sense indicator composition may be used to determine a loss of smell and/or taste of an individual (e.g., subject) in relation to a particular corner of the four components of taste or smell.

For example, the sense indicator composition may comprise one or more active ingredients having a taste and/or smell property and one or more non-active ingredients. The active ingredient may include a concentration of an agent (e.g., flavoring agent and/or odor agent) that is sufficient for detection of the odor and/or taste properties of that active ingredient. The active ingredient may include taste (flavor) and/or odor (smell) properties relating to one of the four components of taste and/or smell (salt, sweet, sour, bitter). Thus, an individual's inability to taste and/or smell the flavor and/or odor properties when the sense indicator composition is provided to them may indicate a loss of sense of smell and/or taste. That loss of smell and/or taste may indicate a symptom of a medical condition or disease, such as those discussed further above. The one or more active ingredients also may be of sufficient quality to impart a particular flavor (taste) and/or odor (smell) property. The taste property may involve one or more natural and/or artificial chemicals that provide a particular flavor characteristic/property; the smell property may involve one or more natural and/or artificial chemicals that provide a particular fragrant characteristic/property.

While the examples discussed below (Tables 1-7) provide for specific types of flavor and smell characteristics or properties (e.g., watermelon, vanilla, mint, coffee), any combination of smells and tastes can be used. For example, the flavor and smell characteristics or properties may be selected to portray one or more of salt, sweet, sour, and bitter characteristics or properties. Further, the flavor and smell characteristics or properties can be tailored to specific regions or local perception of tastes and smells. Individuals living in particular regions or locations may be more familiar with certain tastes and smells compared to individuals living in a different region or location. For example, an individual from one country may be familiar with the taste of a watermelon, while one living in another country may be more familiar with the taste of a papaya.

The one or more non-active (or inactive) ingredients may be used to preserve the taste (flavor) and smell (odor) characteristics or properties of the one or more active ingredients in the sense indicator composition. For example, the composition may remain stable over an extended period of time (e.g., one year after exposing the composition to ambient atmosphere) due to preservative capabilities imparted by the one or more non-active ingredients. The one or more non-active ingredients may also assist in preventing the taste (flavor) and smell (odor) characteristics or properties of the one or more active ingredients from changing/altering over time. The changing/altering of one or more of the taste (flavor) and smell (odor) characteristics or properties of the one or more active ingredients in the sense indicator composition may result in an unreliability of the individual's (subject's) response to being provided with the sense indicator composition. For example, if the taste and smell characteristics or properties of the sense indicator composition change over time, then an individual's response changing over time cannot be isolated to a change in the individual's sense of smell and/or taste over time, because the taste and smell characteristics or properties of the sense indicator composition are also changing over time. Thus, the ingredients of the sense indicator composition may contribute to improvements over traditional systems and methods by providing the embodiments disclosed herein with the ability to reproduce the same odor and/or taste properties over time/multiple uses.

Non-limiting examples of sense indicator compositions and their ingredients are provided below.

TABLE 1

Sense indicator composition (Example 1)

| Ingredient | Concentration |
| --- | --- |
| Active ingredients: Sense indicator | 3% or less |
| Inactive ingredients: Non-sense indicator | 97-99.9% |

TABLE 2

Sense indicator composition (Example 2)

| Ingredient | Concentration |
| --- | --- |
| Flavoring agent | 3% or less |
| Skin-conditioning agent: emollient, viscosity increasing agent - nonaqueous, emollient, skin conditioning, and viscosity controlling; film former; occlusive; masking agent, and solvent; sweetener | 97-99.9% |

TABLE 3

Sense indicator composition (Example 3)

| Ingredient | Function | Concentration |
| --- | --- | --- |
| Flavoring agent | taste and/or odor properties | 3% or less |
| hydrogenated polyisobutene | skin-conditioning agent - emollient, viscosity increasing agent - nonaqueous, emollient, skin conditioning, and viscosity controlling | 80-90% |
| ethylene/propylene/styrene copolymer butylene/ethylene/styrene copolymer | viscosity increasing agent - nonaqueous film former and film forming | 3-10% |
| cocos nucifera (coconut) oil | skin-conditioning agent- miscellaneous; skin-conditioning agent - occlusive, emollient, masking, skin conditioning, and solvent | 5% or less |
| stevioside (steviol glycoside) | sweetener | 5% or less |

TABLE 4

Sense indicator composition (Example 4)

| Ingredient | Function | Concentration |
| --- | --- | --- |
| Watermelon flavoring agent | taste and/or odor properties of watermelon | 3% or less |
| hydrogenated polyisobutene | skin-conditioning agent - emollient, viscosity increasing agent - nonaqueous, emollient, skin conditioning, and viscosity controlling | 80-90% |
| ethylene/propylene/styrene copolymer butylene/ethylene/styrene copolymer | viscosity increasing agent - nonaqueous film former and film forming | 3-10% |
| cocos nucifera (coconut) oil | skin-conditioning agent- miscellaneous; skin-conditioning agent - occlusive, emollient, masking, skin conditioning, and solvent | 5% or less |
| stevioside (steviol glycoside) | sweetener | 5% or less |

TABLE 5

Sense indicator composition (Example 5)

| Ingredient | Function | Concentration |
| --- | --- | --- |
| Vanilla flavoring agent | taste and/or odor properties of vanilla | 3% or less |
| hydrogenated polyisobutene | skin-conditioning agent - emollient, viscosity increasing agent - nonaqueous, emollient, skin conditioning, and viscosity controlling | 80-90% |
| ethylene/propylene/styrene copolymer butylene/ethylene/styrene copolymer | viscosity increasing agent - nonaqueous film former and film forming | 3-10% |
| cocos nucifera (coconut) oil | skin-conditioning agent- miscellaneous; skin-conditioning agent - occlusive, emollient, masking, skin conditioning, and solvent | 5% or less |
| stevioside (steviol glycoside) | sweetener | 5% or less |

TABLE 6

Sense indicator composition (Example 6)

| Ingredient | Function | Concentration |
| --- | --- | --- |
| Mint flavoring agent | taste and/or odor properties of mint | 3% or less |
| hydrogenated polyisobutene | skin-conditioning agent - emollient, viscosity increasing agent - nonaqueous, emollient, skin conditioning, and viscosity controlling | 80-90% |
| ethylene/propylene/styrene copolymer butylene/ethylene/styrene copolymer | viscosity increasing agent - nonaqueous film former and film forming | 3-10% |
| cocos nucifera (coconut) oil | skin-conditioning agent- miscellaneous; skin-conditioning agent - occlusive, emollient, masking, skin conditioning, and solvent | 5% or less |
| stevioside (steviol glycoside) | sweetener | 5% or less |

TABLE 7

Sense indicator composition (Example 7)

| Ingredient | Function | Concentration |
| --- | --- | --- |
| Coffee flavoring agent | taste and/or odor properties of coffee | 3% or less |
| hydrogenated polyisobutene | skin-conditioning agent - emollient, viscosity increasing agent - nonaqueous, emollient, | 80-90% |

TABLE 7-continued

Sense indicator composition (Example 7)

| Ingredient | Function | Concentration |
|---|---|---|
| ethylene/propylene/styrene copolymer | skin conditioning, and viscosity viscosity increasing agent - nonaqueous | 3-10% |
| butylene/ethylene/styrene copolymer | film former and film forming | |
| cocos nucifera (coconut) oil | skin-conditioning agent - miscellaneous; skin conditioning agent - occlusive, emollient, masking, skin conditioning, and solvent | 5% or less |
| stevioside (steviol glycoside) | sweetener | 5% or less |

In some embodiments, the sense indicator composition may be single use. In other embodiments, the sense indicator composition may be multiple use. For example, the sense indicator composition, consistent with embodiments disclosed herein, may be used, when administered periodically or over time, to identify a baseline of an individual's taste and smell. As such, periodic assessments may allow for tracking taste and smell changes, both taste and/or smell deteriorations or taste and/or smell improvements, both physiologically and neurologically over time when, for example, being compared to initial baseline scores.

Figure 4:
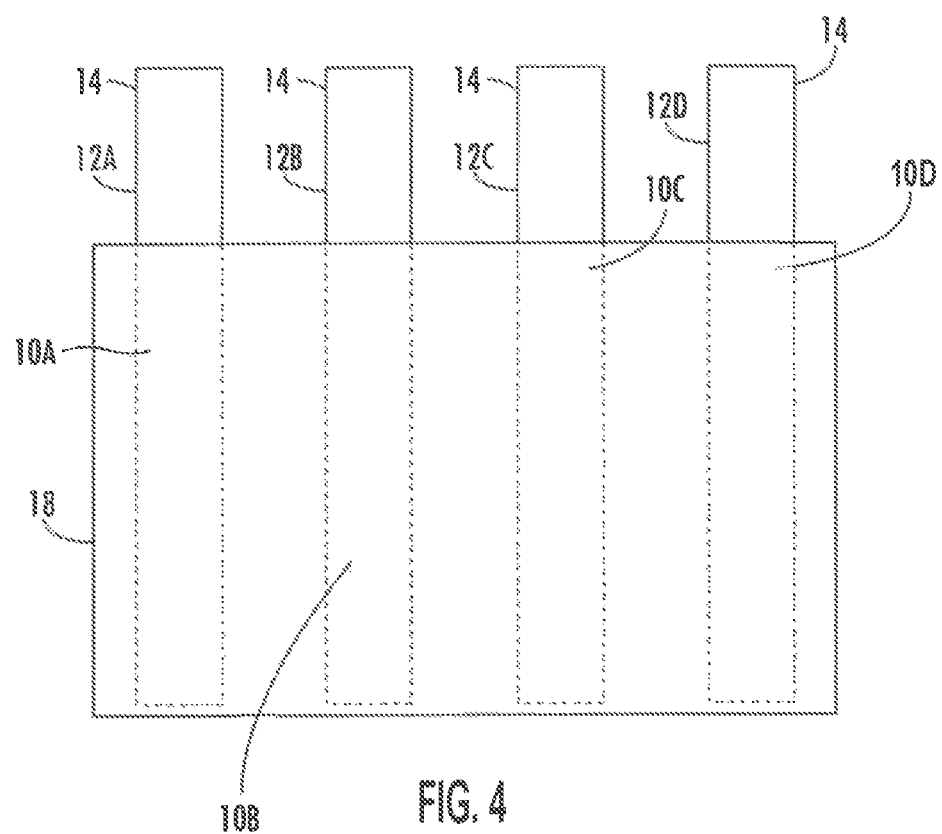
FIG. 4 illustrates an example kit including multiple sense indicator devices, each having a composition with a different taste/smell property, consistent with embodiments of the present disclosure.

FIG. 4 illustrates an example kit 18 including multiple sense indicator devices 10A, 10B, 10C, 10D. As shown in FIG. 4, four sense indicator devices 12A, 12B, 12C, 12D may be provided in kit 18, and each sense indicator device 12A, 12B, 12C, 12D may correspond to a particular taste and/or smell property of the four components of taste and/or smell (salt, sweet, sour, bitter). For example, sense indicator device 12A may include sense indicator composition 10A that has salt taste and/or smell properties; sense indicator device 12B may include sense indicator composition 10B that has sweet taste and/or smell properties; sense indicator device 12C may include sense indicator composition 10C that has sour taste and/or smell properties; and sense indicator device 12D may include sense indicator composition 10D that has bitter taste and/or smell properties. For example, sense indicator composition 10A may include a flavoring agent that has a particular, predetermined (e.g., relatively higher) concentration of sodium chloride or other agents, eliciting a salt taste and/or smell property. Sense indicator composition 10B may include a flavoring agent that has another particular, predetermined (e.g., relatively higher) concentration of carbohydrates (e.g., glucose, sucrose, fructose), eliciting a sweet taste and/or smell property. Sense indicator composition 10C may include a flavoring agent that has yet another particular, predetermined (e.g., relatively higher) concentration of acetic acid or other agents, eliciting a sour taste and/or smell property. Further, sense indicator composition 10D may include a flavoring agent that has still another particular, predetermined (e.g., relatively higher) concentration of phenols and/or polyphenols and/or tartaric acid, eliciting a bitter taste and/or smell property. In some embodiments, sense indicator composition 10A may have taste and/or smell properties of watermelon; sense indicator composition 10B may have taste and/or smell properties of vanilla; sense indicator composition 10C may have taste and/or smell properties of mint; and sense indicator composition 10D may have taste and/or smell properties of coffee. Further, each sense indicator device 10A, 10B, 10C, 10D may include a housing 14. Each sense indicator device 12A, 12B, 12C, 12D may be provided to an individual (subject) during each assessment to evaluate whether the individual can detect each of the taste and/or smell properties and then determine what each of the taste and/or smell properties represent (e.g., salt, sweet, sour, bitter).

Figure 5:
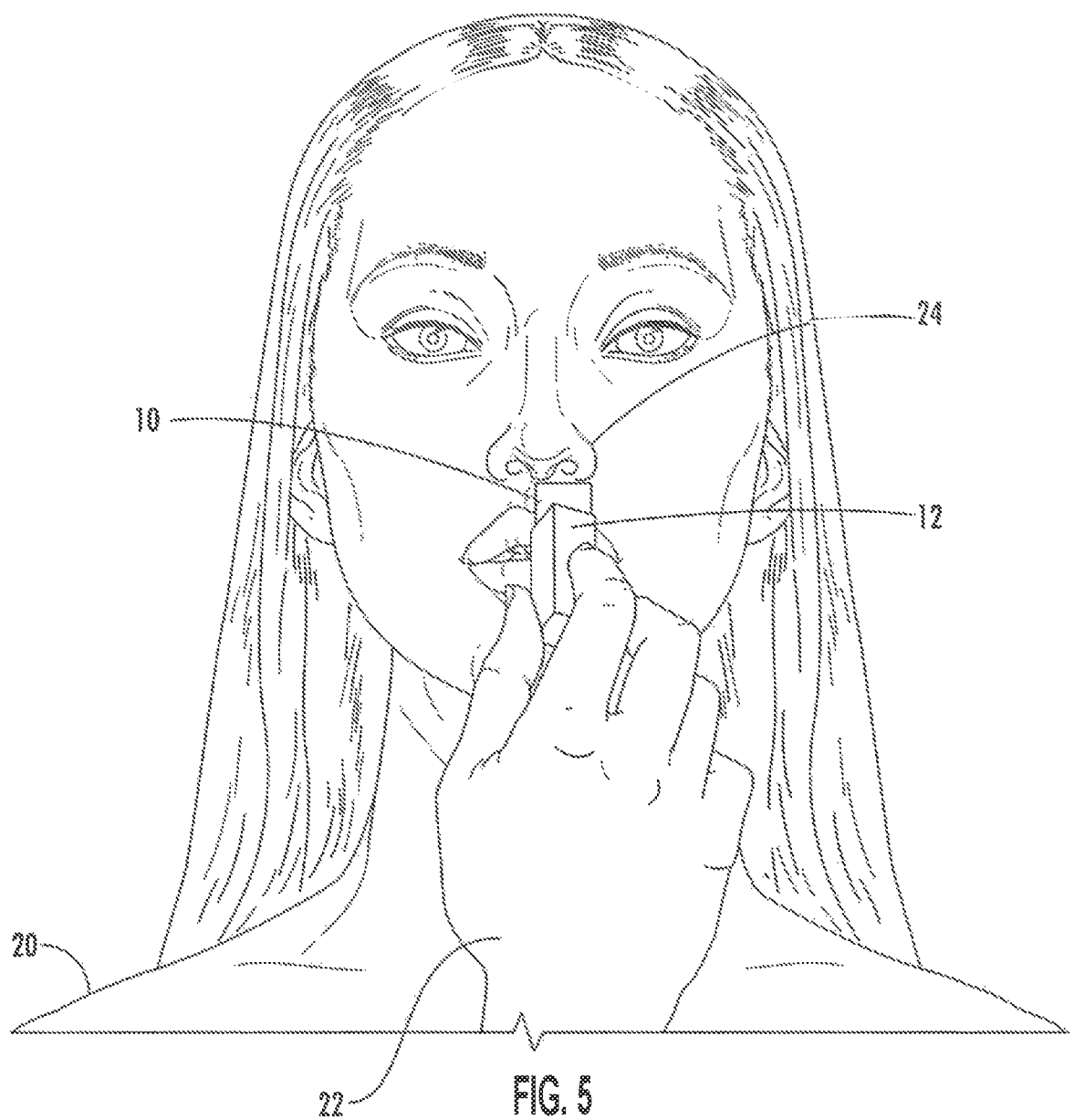
FIG. 5 illustrates an example of providing the sense indicator device of FIG. 1 to an individual's (e.g., subject's) nose, consistent with embodiments of the present disclosure.
Figure 6:
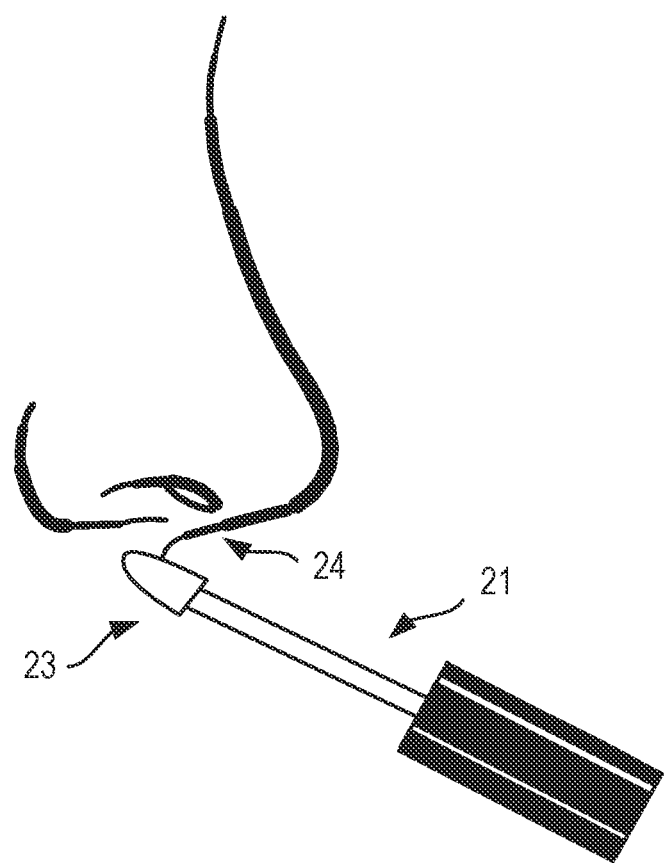
FIG. 6 illustrates a side view of providing the sense indicator device to an individual's (e.g., subject's) nose, consistent with embodiments of the present disclosure.
Figure 7:
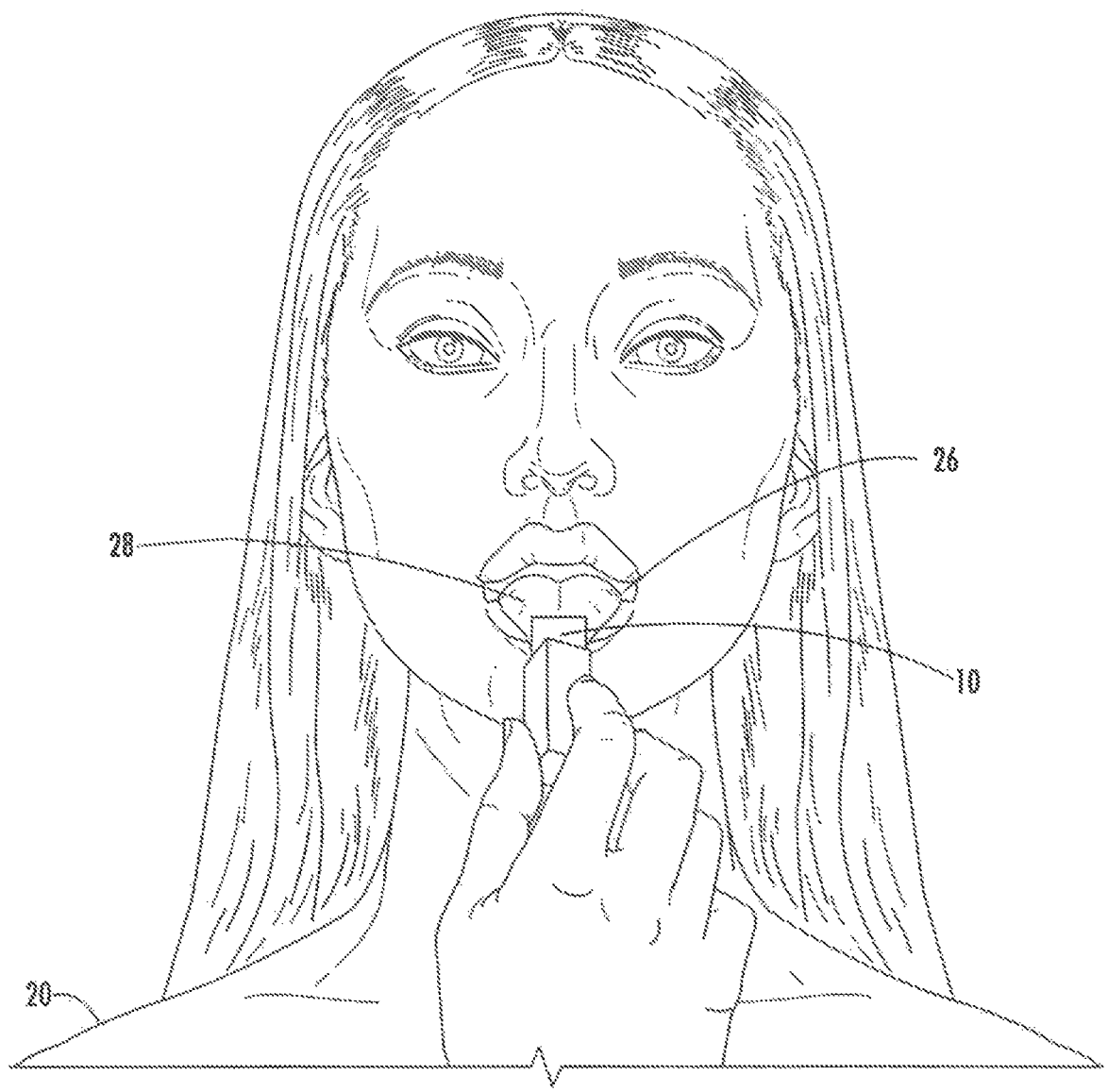
FIG. 7 illustrates an example of providing the sense indicator device of FIG. 1 to an individual's (e.g., subject's) mouth, consistent with embodiments of the present disclosure.
Figure 8:
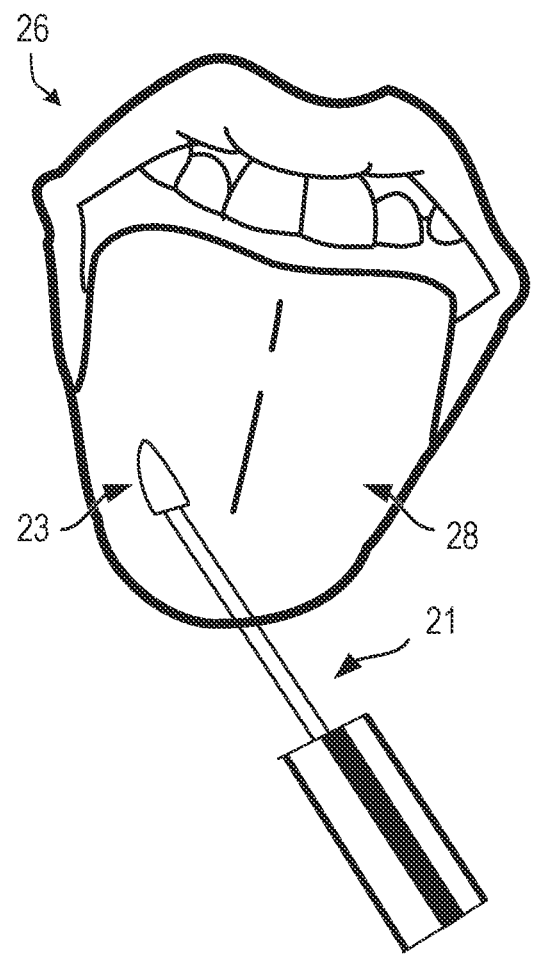
FIG. 8 illustrates an example of providing the sense indicator device to the anterior two-thirds of an individual's (e.g., subject's) tongue, consistent with embodiments of the present disclosure.

FIGS. 5-8 provide examples of providing a sense indicator device 12, which includes a sense indicator composition 10, to the nose (as shown in FIGS. 5 and 6) and mouth (as shown in FIGS. 7 and 8) of an individual.

As shown in FIGS. 5 and 6, the sense indicator composition may be held below a nostril 24 of the individual 20, where the individual 20 may be holding in their hand 22 the sense indicator device 12 below their nostril 24. The individual 20, with their mouth closed, may place the sense indicator device 12 (the composition 10 itself, as shown in FIG. 5, or the composition 10 on an applicator, as shown in FIG. 6) directly beneath a nostril for a period of time (e.g., five seconds). The individual 20 may provide a response that includes: (1) whether they detect that there is a smell; and (2) an identification of what the smell is (e.g., salt, sweet, sour, bitter).

Additionally or alternatively, as shown in FIGS. 7 and 8, the individual 20 may provide the sense indicator device (the composition 10 itself or the composition 10 on an applicator) to their mouth 26 with or without their nose clamped. The composition 10 may be applied to the anterior two-thirds of the tongue 28 (as shown in FIGS. 7 and 8) or on their lips (in which case the individual 20 may then lick their lips to taste the composition 10). The individual 20 may provide a response that includes: (1) whether they detect that there is a taste; and (2) an identification of what the taste is (e.g., salt, sweet, sour, bitter).

It is contemplated that the identification of what individual 20 is smelling or tasting can include different terms that apply to each corner of the four components of taste and smell. For example, a response indicative of salt may involve any one or more of the following descriptors: watermelon, fresh, green, juicy, fruity, salt. A response indicative of sweet may involve any one or more of the following descriptors: vanilla, warm, woodsy, comforting, sugar, sweet. A response indicative of sour may involve any one or more of the following descriptors: mint, herbal, cool, refreshing, tart, sour. A response indicative of bitter may involve any one or more of the following descriptors: coffee, acidic, aromatic, nutty, awakening, unsweetened, bitter.

FIGS. 9-11 illustrate example scorable system evaluation sheets. The example scorable system evaluation sheets may be provided as physical papers or electronic records. FIG. 9 illustrates an example scorable system evaluation sheet for acute clinical assessments. The scorable system evaluation sheet of FIG. 9 can be used in evaluating acute medical conditions such as, but not limited to, concussions in sports. For example, after a blow to the head while playing a sport, an individual may be assessed using the kits disclosed herein to determine potential head trauma. An assessment administrator (e.g., healthcare provider) may provide each sense indicator device to the individual in the manner discussed above (to their nose and to their mouth) with respect to FIGS. 5-8, with the taste and/or odor property corresponding to each sense indicator device being unknown to the individual being assessed. The individual may then determine, based on smelling or tasting the sense indicator composition of each sense indicator device, whether they detect a smell or taste and, if so, what they are smelling or tasting.

The detection and identification of the smell or taste may be recorded by positive and negative responses. A positive response ("1") may include a detection of a smell or taste property, and a negative response ("0") may include a lack of detection of a smell or taste property. For example, a positive response may pertain to an individual detecting that they taste or smell something, and a negative response may pertain to the individual failing to smell or taste anything. Further, a positive response ("1") may include a correct identification of the smell or taste property, and a negative response ("0") may include an incorrect identification of the smell or taste property. For example, a positive response may pertain to an individual correctly identifying what the designated taste or smell property of the particular sense indicator composition is (e.g., salt, sweet, sour, bitter), and a negative response may pertain to the individual incorrectly identifying what the designated taste or smell property of the particular sense indicator composition is.

The kit may be provided to the individual in different environments (e.g., on the athletic field, in the medical tent, in the locker room, in a combat environment) to both track the progression of the individual's sense of taste and/or smell over time, and/or to evaluate the individual's sense of taste and/or smell in different environments (because the ambient environment may impact the detection and identification of a particular smell/taste).

FIG. 10 illustrates an example scorable system evaluation sheet for periodic evaluations. As shown in FIG. 10, the individual's olfactory and gustatory totals (which would be in a range from 0-8 in the depicted example) of the responses to the scorable system evaluation sheet of FIG. 9 may be recorded on the evaluation sheet of FIG. 10. The individual may then undergo exams at later dates (shown by the columns labeled "EXAM DATE") to track any changes (improvements or deteriorations) in the individual's sense of smell and/or taste. The olfactory and gustatory totals may be evaluated and calculated in a similar manner to those discussed above with respect to FIG. 9, and then tracked in the periodic evaluation record shown in FIG. 10.

FIG. 11 illustrates an example scorable system evaluation system for chronic evaluations. As shown in FIG. 11, an assessment administrator (e.g., healthcare provider) may provide each sense indicator device to the individual in the manner discussed above (to their nose and to their mouth) with respect to FIGS. 5-8, with the taste and/or odor property corresponding to each sense indicator device being unknown to the individual being assessed. The individual may then determine, based on smelling or tasting the sense indicator composition of each sense indicator device, whether they detect a smell or taste and, if so, what they are smelling or tasting. The detection and identification of smell or taste may be recorded by positive and negative responses. The assessment administrator may record a positive response as a ("1") and a negative response as a ("0"). A positive response ("1") may include a detection of a smell or taste property, and a negative response ("0") may include a lack of detection of a smell or taste property. For example, a positive response may pertain to an individual detecting that they taste or smell something, and a negative response may pertain to the individual failing to smell or taste anything. Further, a positive response ("1") may include a correct identification of the smell or taste property, and a negative response ("0") may include an incorrect identification of the smell or taste property. For example, a positive response may pertain to an individual correctly identifying what the designated taste or smell property of the particular sense indicator composition is (e.g., salt, sweet, sour, bitter), and a negative response may pertain to the individual incorrectly identifying what the designated taste or smell property of the particular sense indicator composition is. The examination may be administered multiple times on different dates, and each date of examination may be recorded in the column labeled "Examination Date." Further, olfactory subtotals and gustatory subtotals may also be recorded. Thus, the individual's changes in smell and/or taste may be tracked over time, and a deterioration or improvement in their smell and/or taste may be evaluated/shown.

This objective and reliable evaluation of an individual's sense of smell and/or taste over time may provide an early prediction or diagnosis of various cognitive or sensory disorders (e.g., Parkinson's disease, Alzheimer's disease) where early detection may provide a window of opportunity (e.g., 10-15 years) prior to a confirmed identification of its presence (e.g., a presence of amyloid plaques in the brain) as detected by other modalities (e.g., MRI, CT). This window of opportunity may provide a time frame for development and administration of preventative pharmacological therapeutics and other modes of treatment that may delay and/or prevent further cognitive deterioration. Periodic, continued use by individuals (subjects) who exhibit a loss or diminished ability to accurately detect and/or identify one or more of these core tastes or odorants (e.g., one of the four discussed above as the four components of taste and/or smell) can, in some embodiments, provide noxious stimulation to assist in regaining (or recovering) both perception and identification of these taste and/or odor properties. Further, embodiments of the present disclosure may be used to identify particular smell and/or taste properties that an individual is unable to detect and/or identify, which may be indicative of a deficiency of a particular nutrient (or malnutrition). Thus, embodiments of the present disclosure may be used in tandem with, for example, chemotherapy as an indicator of particular nutritional (e.g., vitamin, mineral) deficiencies that may be caused by, for example, heavy metal chemotherapy drugs. Additionally, or alternatively, some embodiments of the present disclosure may be used to evaluate and develop drug treatments for various neurological disorders and diseases.

Early use of the sense indicator devices, sense indicator compositions, and/or the scoring systems with evaluation sheets disclosed herein can objectively, and without bias, document and score the onset of various neurological and cerebral medical conditions. Subsequent periodic use of the sense indicator devices, sense indicator compositions, and/or the scoring systems with evaluation sheets disclosed herein can provide documentation of improvements or deterioration of cognition and/or identification of smell and/or taste properties corresponding to the four components of smell and/or taste. In some embodiments, devices, systems, and methods disclosed herein may also be in medical cohort research studies. In contrast to existing devices, systems, and methods, which examine diagnostic biomarkers that do not change over time, olfactory and gustatory functions can change with improvements in clinical condition and have wide-ranging promise as an early diagnostic biomarker as well as an indicator of clinical improvement.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. While certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Throughout this application, various embodiments of the present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numeric values within that range. For example, description of a range such as from 1 to 6 should be considered to include subranges such as from 1 to 3, from 1 to 4, from 1 to 5, from 2 to 4, from 2 to 6, from 3 to 6, and so forth, as well as individual numbers within that range, for example, 1, 2, 3, 4, 5, and 6. This applies regardless of the breadth of the range.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A sense indicator kit, the sense indicator kit comprising:
   a plurality of sense indicator devices, each sense indicator device comprising:
      a housing;
      a composition stored within the housing, the composition including:
         one or more active ingredients including a flavoring agent; and
         one or more inactive ingredients including a preservative configured to keep the composition stable and preserve a smell or taste characteristic associated with the flavoring agent; and
      an applicator, the applicator including an applicator tip, configured to:
         remove a predetermined amount of the composition from the housing; and
         deliver the predetermined amount of the composition to one or more of a nose and a mouth of a subject,
         wherein the housing includes a back pressure mechanism configured to apply a pressure on the applicator tip as the applicator is withdrawn from the housing to control an amount of the composition that remains on the applicator tip when the applicator is withdrawn from the housing, wherein the back pressure mechanism includes a narrow channel in the housing being diametrically smaller than a width of the applicator tip, and wherein the predetermined amount is selected based on a minimum amount of the composition that induces an identification of the smell or the taste characteristic by a healthy subject; and
   one or more evaluation sheets for recording a detection and an identification of the smell or the taste characteristic associated with each sense indicator device by the subject.

2. The sense indicator kit of claim 1, wherein the one or more active ingredients is in a concentration less than or equal to 3% and the one or more inactive ingredients is in a concentration greater than or equal to 97%.

3. The sense indicator kit of claim 1, wherein the one or more inactive ingredients included in the composition includes one or more of: a viscosity increasing agent, a viscosity controlling agent, a film former, an occlusive, a masking agent, a solvent, and a sweetener.

4. The sense indicator kit of claim 3, wherein the composition includes:
   the flavoring agent in a concentration of less than or equal to 3%;
   the viscosity increasing agent in a concentration of 3-10%; and
   the sweetener in a concentration of less than or equal to 5%.

5. The sense indicator kit of claim 1, wherein the applicator tip is a sponge tip.

6. The sense indicator kit of claim 1, wherein the plurality of sense indicator devices includes: a first sense indicator device where the flavoring agent includes a salty taste and odor property; a second sense indicator device where the flavoring agent includes a sour taste and odor property; a third sense indicator device where the flavoring agent includes a sweet taste and odor property; and a fourth sense indicator device where the flavoring agent includes a bitter taste and odor property.

7. The sense indicator kit of claim 1, wherein each sense indicator device is configured to be administered to the subject by an administrator, and wherein the administrator records a response by the subject on the one or more evaluation sheets to determine one or more of a loss of smell and a loss of taste in the subject.

8. The sense indicator kit of claim 7, wherein the determined one or more of the loss of smell or the loss of taste in the subject is a symptom indicative of one or more of a viral infection, a concussion, a brain injury, Parkinson's disease, Alzheimer's disease, epilepsy, dementia, cystic fibrosis, diabetes, multiple sclerosis, breast cancer metastasis, or a nutritional deficiency.

9. The sense indicator kit of claim 1, wherein the sense indicator device is configured to stimulate recovery of one or more of a loss of smell and a loss of taste in the subject.

10. The sense indicator kit of claim 1, wherein the predetermined amount is selected based on a maximum amount of the composition for the composition to be used multiple times over a period of time.

11. The sense indicator kit of claim 1, wherein the applicator tip is angled and the amount of the composition that remains on the applicator tip is controlled by an angle of the applicator tip.

12. The sensor indicator kit of claim 1, wherein the back pressure mechanism is configured to create friction upon a mating of the narrow channel in the housing and the applicator tip as the applicator tip is withdrawn from the housing, removing an excess amount of the composition to control the amount of composition that remains on the applicator tip.

13. A method for determining one or more of a loss of taste and a loss of smell in a subject using the sense indicator kit of claim 1, the method comprising:
  administering the sense indicator kit to the subject, the administration comprising providing each sense indicator device of the plurality of sense indicator devices to the subject by:
    removing the applicator of the sense indicator device from the housing;
    providing the applicator to one or more of a nose and a mouth of the subject; and
    recording, on the one or more evaluation sheets, a response of the subject each time the applicator is provided to the one or more of the nose and the mouth of the subject; and
  determining, using the recorded responses on the one or more evaluation sheets, one or more of a loss of smell and a loss of taste of the subject.

14. The method of claim 13, further comprising providing the sense indicator device to the one or more of the nose and the mouth of the subject at predetermined intervals to stimulate recovery of the one or more of the loss of smell or the loss of taste in the subject.

15. The method of claim 13, further comprising providing the applicator to the one or more of the nose and the mouth of the subject at predetermined intervals to identify changes in a sense of smell or a sense of taste of the subject over time.

16. The method of claim 15, further comprising
  identifying the changes in the sense of smell or the sense of taste of the subject over time based on a change in the response.

17. The method of claim 13, wherein the determined one or more of the loss of smell and the loss of taste is a symptom indicative of one or more of a viral infection, a concussion, a brain injury, Parkinson's disease, Alzheimer's disease, epilepsy, dementia, cystic fibrosis, diabetes, multiple sclerosis, breast cancer metastasis, or a nutritional deficiency.

18. The method of claim 13, wherein the providing the applicator to the mouth of the subject includes applying the predetermined amount of the composition to one or more of a tongue and lips of the subject.

19. The method of claim 13, wherein providing the applicator to the nose of the subject includes holding the applicator below a nostril of the subject.

20. The method of claim 12, wherein the tip of the applicator is angled, and wherein the predetermined amount of the composition remains on the angled tip of the applicator upon removal of the applicator from the housing.

21. The method of claim 13, wherein the tip of the applicator includes a sponge material.

22. The method of claim 13, wherein the response of the subject is scored based on one or more positive and/or negative responses.

* * * * *

UNITED STATES PATENT AND TRADEMARK OFFICE
CERTIFICATE OF CORRECTION

| | | |
|---|---|---|
| PATENT NO. | : 12,402,829 B2 | Page 1 of 1 |
| APPLICATION NO. | : 18/620839 | |
| DATED | : September 2, 2025 | |
| INVENTOR(S) | : Ira Schneider et al. | |

It is certified that error appears in the above-identified patent and that said Letters Patent is hereby corrected as shown below:

On the Title Page

Item (57) Abstract, Line 2, "subject." should read as --subject--.

Item (57) Abstract, Line 7, "salt," should read as --salty,--.

Signed and Sealed this
Eleventh Day of November, 2025

John A. Squires
*Director of the United States Patent and Trademark Office*